United States Patent [19]
Oliver

[11] Patent Number: 5,869,062
[45] Date of Patent: Feb. 9, 1999

[54] SKIN TREATMENT COMPOSITION

[76] Inventor: Benjamin Oliver, 811 Flushing Ave. Apt. 15-E, Bklyn., N.Y. 11206

[21] Appl. No.: 863,733

[22] Filed: May 27, 1997

[51] Int. Cl.⁶ .................. A61K 35/78; A61K 39/385; A61K 33/32

[52] U.S. Cl. .................. 424/195.1; 424/616; 424/641; 514/458; 514/474; 514/557; 514/714; 514/725; 514/859

[58] Field of Search .................. 424/195.1, 616, 424/641; 514/458, 474, 557, 714, 725, 85.9

[56] References Cited

U.S. PATENT DOCUMENTS

| | | |
|---|---|---|
| 4,255,418 | 3/1981 | Bailey . |
| 4,331,653 | 5/1982 | Brown et al. . |
| 4,428,933 | 1/1984 | King . |
| 4,645,668 | 2/1987 | Pinnell . |
| 4,855,138 | 8/1989 | Trenzeluk . |
| 5,445,823 | 8/1995 | Hall et al. . |

OTHER PUBLICATIONS

Merck Index, 11$^{th}$ ed, p. 248, ¶1636, 1989.

*Primary Examiner*—Leonard Schenkman

[57] ABSTRACT

An improved skin treatment composition is provided. The composition comprises calamine in an amount between about 8% and 20%, an antioxidant in an amount between about 0.05 and 3 weight percent; and an herbal anti-bacterial substance in an amount between about 0.25 and 4 weight percent. These ingredients are combined with a base, preferably comprised of water and glycerin, in order to prepare the inventive composition. The base will generally comprise from between 25% and 60% by weight of the overall composition.

20 Claims, No Drawings

SKIN TREATMENT COMPOSITION

BACKGROUND OF THE INVENTION

This invention relates to a skin treatment composition, and more particularly, to a skin treatment composition which clears up most skin-related problems naturally and without any side effects.

There are many skin-related problems from which various individuals suffer. One obvious such problem is acne, which primarily afflicts teenagers and young adults. Other skin problems include rashes, blemishes, skin bites, razor irritation, athlete's foot, and general itching.

In the prior art, there are many old and current methods which are suitable for treating an individual's skin. One common such material is alpha hydroxy acids, which is used to treat acne and which is found in many well known products. However, the use of alpha hydroxy acids is less than desirable, since it can in fact cause itching and redness on sensitive skin. Moreover, while alpha hydroxy acid is somewhat successful in the treatment of acne, it has the disadvantage during treatment of making the acne worse before making it better.

Another common skin treatment medication is benzoyl peroxide, which is also used for treating acne and is found in such products as OXY-10. This composition suffers from the same disadvantages as alpha hydroxy acids.

These and other known methods have the general disadvantages of not working fast, of not covering a broad spectrum of skin-related problems, and being somewhat expensive to purchase.

Accordingly, it would be desirable to provide a skin treatment composition which overcomes the above disadvantages, and which is safe to use, is effective on a broad range of skin problems, and which is inexpensive to manufacture.

SUMMARY OF THE INVENTION

Generally speaking, in accordance with the invention, there is provided an improved skin treatment composition. The composition comprises calamine in an amount between about 8% and 20%, an antioxidant in an amount between about 0.05 and 3 weight percent, and an herbal anti-bacterial substance in an amount between about 0.25 and 4 weight percent. These ingredients are combined with a base, preferably comprised of water and glycerin, in order to prepare the inventive composition. The base will generally comprise from between 25% and 60% by weight of the overall composition.

In addition, the inventive composition may also include one or more astringents as well as a peroxide component.

There are a number of advantages in using the inventive skin treatment composition. In the first place, the composition does not cause any side effects. Additionally, when applied, it works substantially faster than other skin treatment compositions. Further, it is an all-natural composition and only incorporates natural ingredients. Moreover, the inventive composition is not restricted in its application. The inventive composition can be used for acne, rashes, blemishes, general itching, chicken pox, athlete's foot, etc.

Accordingly, it is an object of the invention to provide an improved skin treatment composition.

Still another object of the invention is to provide a skin treatment composition which is suitable for use in treating a broad range of skin-related problems.

Still a further object of the invention is to provide an improved skin formulation, which, when applied, works quickly and without any side effects.

Yet a further object of the invention is to provide an improved skin treatment composition which only incorporates natural ingredients.

Still other objects and advantages of the invention will in part be obvious and will in part be apparent from the following description.

The invention accordingly comprises a composition possessing the features, properties and relation of elements, which are exemplified in the following detailed disclosure, and the scope of the invention will be indicated in the claims.

BRIEF DESCRIPTION OF THE PREFERRED EMBODIMENTS

The inventive skin treatment composition includes calamine, which is zinc oxide with approximately 0.5% ferric oxide, in an amount between about 8 and 20 weight percent. The purpose of the calamine ingredient is for reducing inflammation, redness and itching, as well as for drying out excess oils and fluids.

A second required ingredient or component in the inventive composition is the use of at least one anti-oxidant in an amount between about 0.05 and 3 weight percent. An anti-oxidant is a nutrient which prevents free radical damage to skin cells. Suitable anti-oxidants include Vitamin C (ascorbic acid—between 0.45 and 2 weight percent), Vitamin E (between 0.08 and 1.0 weight percent) and beta-carotene (Vitamin A).

A third required ingredient in the inventive composition is the use of a naturally occurring anti-bacterial product in an amount between about 0.25 and 4 weight percent. The purpose of including an anti-bacterial product in the inventive formulation is for treating any infections which may arise. Suitable naturally occurring anti-bacterial products include naturally occurring herbs selected from golden seal extract, tea tree oil (melalence alternifolia), echinacea (angustifolia pururea), garlic, and red clover. The preferred anti-bacterial products are golden seal extract (0.35–0.90 weight percent) and tea tree oil (1 to 3 weight percent). Golden seal extract itself includes albumin, berberine, biotin, calcium, candine, chlorine, choline, chologenic acid, fat, hydrastine, inositol, iron, lignini manganese, volatile and essential oils, PABA, phosphorus, potassium, resin, starch, sugar, B complex and vitamins. The key components of golden seal extract are choline, chologenic acid and B Complex, since they function to facilitate the infection fighting ability of the herbal ingredients.

The inventive composition is prepared using a base comprising water in an amount between about 15 and 35 weight percent, and a diluent such as glycerin or propylene glycol in an amount between 10% and 25%. The purpose of including water is to act as a neutralizer. The purpose of including a diluent such as glycerin is to dissolve the ingredients so that a mixture is formed. The base itself should be in an amount between about 25 and 60 weight percent.

The inventive composition may also include the addition of an astringent such as witch hazel (liquid extract from leaves or bark of a hamamelis virginiana plant) and alpha hydroxy acids. An astringent is a material which constricts tissues, thereby diminishing discharge. The purpose of the astringent is to tighten the pores and clean the face. The preferred astringent is witch hazel and the preferred range of the astringent is in an amount between about 1 and 12 weight percent.

The composition of the invention may also include alcohol as a solvent. The purpose of the alcohol solvent is to facilitate mixing of the formulation together. Suitable alcohols include ethyl alcohol and isopropyl alcohol, and the alcohol should be in a range between about 3 and 10 weight percent.

A peroxide may also be added to the inventive formulation in an amount between about 3 and 8 percent. Suitable peroxides include hydrogen peroxide. The purpose of including a peroxide component is to help treat any infection. The peroxide may also be selected from benzoyl peroxide, acetyl peroxide, t-butyl peroxide, para chlorobenzoyl peroxide, and methyl ethyl ketone peroxide.

Zinc oxide may also be included in the inventive formulation. The purpose of zinc oxide is to act as an additional base and the zinc oxide would be in the formulation in an amount between about 8 and 20 weight percent.

The following illustrates an example of the inventive skin treatment composition.

| Actual Range % | |
|---|---|
| $H_2O$ | 25.25% |
| Glycerin | 20.00% |
| Calamine | 18.00% |
| Zinc Oxide | 18.00 |
| Witch Hazel | 5.00% |
| Ascorbic Acid | .88% |
| Peroxide 3% strength | 5.00% |
| Golden Seal | 2.00% |
| ETDH (Sd-40) | 5.00% |
| Tea Tree Oil | .70% |
| Vitamin E (Tocopherol) | .16% |
| | 100.00% |

In order to prepare this composition, water is heated to 83° C., and then cooled in order to kill all bacteria. Then, the glycerin ingredient is added, followed by the zinc oxide. The calamine ingredient is slowly added until a suitable consistency is achieved. Following this, each of the witch hazel, ascorbic acid, peroxide and golden seal extract ingredients is added one at a time into the mixture.

Separately, tea tree oil and the alcohol are mixed until a clear liquid is prepared. This mixture is then added to the main mixture and mixed together. Finally, the vitamin E is added until a desired consistency is achieved.

As can be appreciated, the steps in preparing the application include first combining the calamine with the base ingredients water and glycerin. Thereafter, one adds the anti-oxidant ingredient and the natural or herbal anti-bacterial ingredient, as required.

One of the advantages of the inventive skin treatment composition is that it will not cause any side effects when used. This is because all natural ingredients are used.

In addition, the inventive skin treatment composition works far more quickly than other known compositions. This is because this formulation is the first to combine herbal antibacterial ingredients with antioxidants.

Furthermore, the composition may used for a variety of skin ailments, and is not restricted in terms of application. This is because of the versatility of the herbal ingredients.

Alternatively, an extra strength formulation of the inventive skin treatment composition may be prepared. This formulation would be suitable for those individuals with severe skin problems, or who otherwise are not treated satisfactorily by the main formulation. The extra strength formulation would also include aloe vera gel in an amount between about 0.01 and 0.05 weight percent, in addition to the other ingredients.

In using the inventive skin formulation for treating acne, unlike most applications, the user can first squeeze the whiteheads which develop when the pores of the skin are clogged. Once this is done, the inventive composition may then be applied. In most prior art formulations, if the whitehead is squeezed, a blemish will result. Since the inventive formulation also treats blemishes, the disadvantage of first squeezing the whitehead does not exist. The reason that the formulation is suitable for both treating acne and for removing blemishes is due to the combination of astringents/antioxidants (for blemishes) and for the herbal antibacterials/calamine (for acne).

In use, a small amount of the inventive composition is simply applied to the area of the skin to be treated, either once or twice a day after the user first cleans his or her face with an anti-bacterial cleanser.

It will thus be seen that the objects set forth above, among those made apparent from the preceding description, are efficiently attained, and since certain changes may be made in the above composition and process without departing from the spirit and scope of the invention, it is intended that all matter contained in the above description shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

I claim:

1. A method for the treatment of skin acne comprising the step of applying a composition directly to the skin comprising a base in an amount between about 25 and 60 weight percent, calamine in an amount between about 8 and 20 weight percent, an anti-oxidant in an amount between about 0.5 and 3 weight percent and an herbal anti-bacterial product in an amount between about 0.25 and 4 weight percent.

2. The method of claim 1, wherein the base comprises water in an amount between about 15 and 35 weight percent and a diluent in an amount between about 10 and 25 weight percent.

3. The method of claim 2, wherein the diluent is selected from the group consisting of glycerin and propylene glycol.

4. The method of claim 1, wherein said anti-oxidant is selected from the group consisting of ascorbic acid, tocopherol and beta-carotene.

5. The method of claim 4, wherein ascorbic acid is present in an amount between 0.45 and 2 weight percent, and wherein tocopherol is present in an amount between about 0.08 and 1 weight percent.

6. The method of claim 1, wherein said herbal anti-bacterial product is selected from the group consisting of golden seal extract, tea tree oil, echinacea, garlic, pau d'arco and red clover.

7. The method of claim 6, wherein said anti-bacterial product is tea tree oil in an amount between about 0.35 and 0.90 weight percent, and golden seal extract in an amount between about 1 and 3 weight percent.

8. The method of claim 1, further including an astringent in an amount between about 1 and 12 weight percent.

9. The method of claim 8, wherein said astringent is selected from the group consisting of witch hazel and alpha hydroxy acids.

10. The method of claim 9, wherein said astringent is witch hazel in an amount between about 3 and 10 weight percent.

11. The method of claim 1, further including an alcohol in an amount between about 3 and 10 weight percent.

12. The method of claim 11, wherein said alcohol is selected from the group consisting of ethyl alcohol and isopropyl alcohol.

13. The method of claim 12, wherein said alcohol is ethyl alcohol in an amount between about 3 and 8 weight percent.

14. The method of claim 1, further including a peroxide in an amount between about 3 and 8 weight percent.

15. The method of claim 14, wherein said peroxide is selected from the group consisting of hydrogen peroxide, benzoyl peroxide, acetyl peroxide, t-butyl peroxide, para chlorobenzoyl peroxide, and methyl ethyl ketone peroxide.

16. The method of claim 1, further including zinc oxide in an amount between about 8 and 20 weight percent.

17. The method of claim 1, further including aloe vera gel in an amount between about 0.01 and 0.05 weight percent.

18. A method for the treatment of acne of the skin comprising the steps of:

cleaning an area of the skin with an anti-bacterial cleanser;

applying a small amount of a composition to said area, said composition comprising a base in an amount between about 25 and 60 weight percent; calamine in an amount between about 8 and 20 weight percent; an anti-oxidant in an amount between about 0.5 and 3 weight percent and an herbal anti-bacterial product in an amount between about 0.25 and 4 weight percent.

19. The method of claim 18, wherein said base comprises water and a diluent; said anti-oxidant is selected from the group consisting of ascorbic acid, tocopherol and beta-carotene; and said herbal anti-bacterial product is selected from the group consisting of golden seal extract, tea tree oil, echinacea, garlic, pau d'arco and red clover.

20. The method of claim 19, wherein said composition further includes an astringent in an amount between about 1 and 12 weight percent and selected from the group consisting of witch hazel and alpha hydroxy acids.

* * * * *